April 19, 1955 H. C. SWIM Plant Pat. 1,383
ROSE PLANT
Filed April 15, 1954
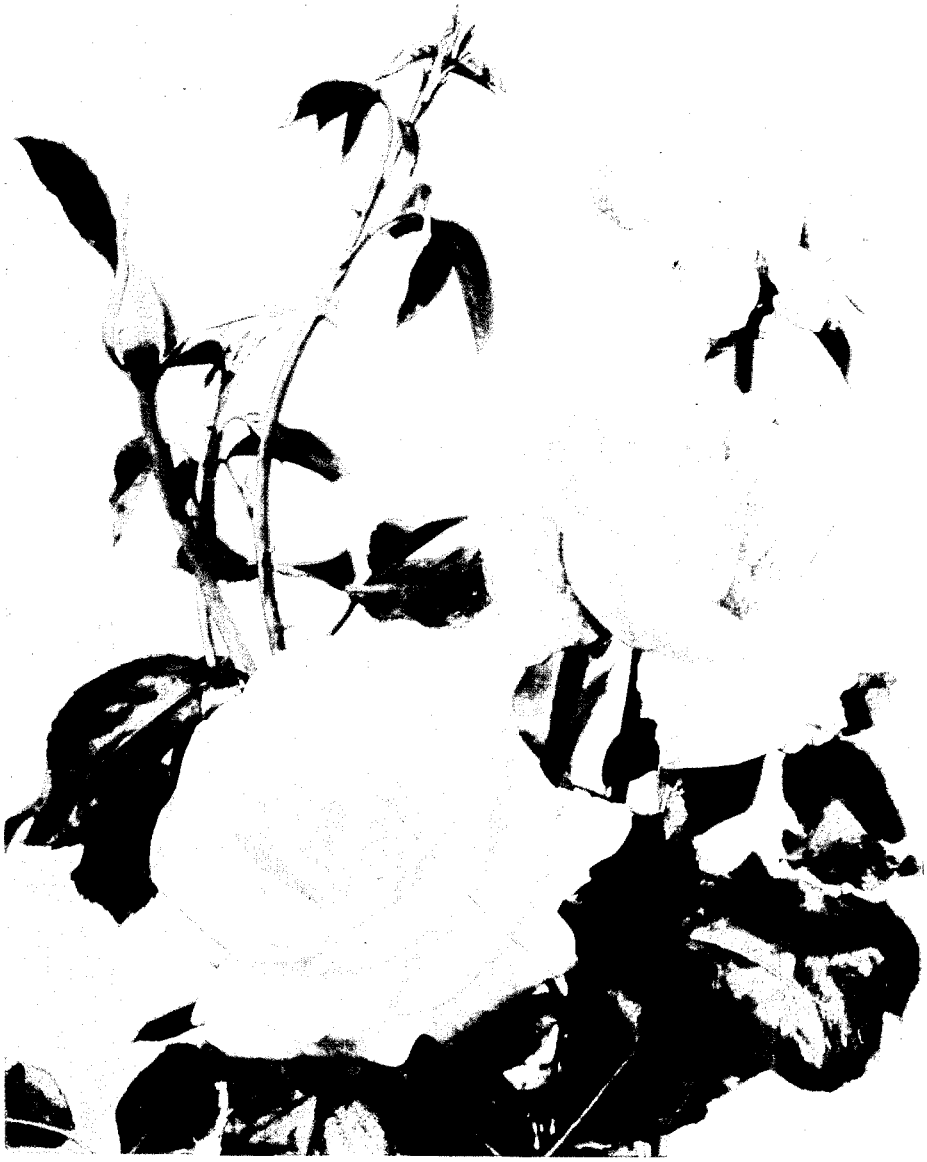
Inventor.
H. C. Swim
By: Robert Cobb
Attorneys.

United States Patent Office

Plant Pat. 1,383

Patented Apr. 19, 1955

1,383

ROSE PLANT

Herbert C. Swim, Ontario, Calif., assignor to Armstrong Nurseries, Inc., Ontario, Calif., a corporation of California Application April 15, 1954, Serial No. 423,549

1 Claim. (Cl. 47—60)

The present invention relates to a new and distinct variety of rose plant of a type which falls between the hybrid tea and hybrid polyantha classes, said new variety having been originated by me as the result of crossing the variety "Fandango" (Plant Patent No. 894) with the variety "Floradora" (unpatented).

The primary objective in making this cross was to produce a new variety which combines the most desirable characteristics of the parent varieties. This objective was fully achieved, as evidenced by the fact that the flowers of my new variety are of a distinctive and unusual shade of salmon red color which is inherited from the parent variety "Floradora"; the flowers approach the size of those of the parent variety "Fandango"; the flowers are produced in abundance throughout the growing season, approaching that of the variety "Floradora"; the petal substance approaches that of "Floradora," with an attendant lasting quality of the flowers which is typical of "Floradora"; the petalage of the flowers is double, falling midway between the petalage of the flowers of the respective parent varieties; and the flowers are borne on long, individual flower stems, which is typical of the variety "Fandango."

In comparison with its seed parent, "Fandango," my new variety is distinguished by the salmon red color of its blooms, whereas the color of the blooms of "Fandango" is bright red and is more popularly described as cherry red; the blooms of my new variety are double in petalage, having 32 to 40 petals, whereas the blooms of "Fandango" are semi-double in petalage and have from 16 to 25 petals; and the petal substance of my new variety is substantially greater than that of "Fandango."

As compared with its pollen parent, "Floradora," my new variety is distinguished by the salmon red color of its blooms, whereas the blooms of "Floradora" are a deeper shade of red, usually described as Scarlet Red, with Nopal Red on the reverse surfaces; the blooms of my new variety are substantially larger in size, measuring from 3½ inches to 4 inches in diameter, whereas the blooms of "Floradora" are much smaller, and measure approximately 2 inches in diameter; the blooms of my new variety are double in petalage, with from 32 to 40 petals, whereas those of "Floradora" are very double in petalage and have from 50 to 55 petals; and the blooms of my new variety are usually produced singly, or sometimes 2 or 3 to a cluster, on relatively long, individual stems, whereas those of "Floradora" are usually produced in clusters of a substantially greater number of blooms and with relatively shorter stems for the individual flowers.

From the foregoing, it will be obvious that my new variety is definitely distinguished from its parents, as well as from all other varieties of its class. Asexual reproduction of my new variety, as performed by budding at Ontario, California, shows that the foregoing characteristics and distinctions come true to form and are established and transmitted through succeeding propagations.

The accompanying drawing shows typical specimens of the flowers and foliage of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"):

Type: Bush; outdoor; seedling; for cut flowers and for garden decoration.

Class: Intermediate between the ordinary hybrid tea and hybrid polyantha classes.

Breeding: Seedling.

*Seed parent.*—"Fandango."

*Pollen parent.*—"Floradora."

Propagation: Holds its distinguishing characteristics through succeeding propagations by budding.

FLOWER

Locality where grown and observed: Ontario, California.

Flowers borne: Sometimes singly and sometimes 2 or 3 to stem; on strong, long stems, with long individual flower stems.

Quantity of bloom: Abundant, outdoors.

Continuity: Continuous during growing season.

Fragrance: Slight.

Bud:

*Peduncle.*—Average length; average caliper to heavy; erect; smooth; few gland-tipped cilia. Color—near Biscay Green, Plate XVII (Ridgway), overlaid with near Mineral Red, Plate XXVII (Ridgway) on side exposed to the sun.

*Before calyx breaks.*—Size—medium. Form—Medium length; ovoid; with foliaceous appendages; some gland-tipped cilia on the surface of the bud; usually with slender, much-cut foliaceous parts extending beyond the tip of the bud equal to ¼ or sometimes more of its length.

*As calyx breaks.*—Color—between Geranium Like, Plate 20, page 20 (Wilson) and Turkey Red, Plate 721, page 94 (Wilson).

*Sepals.*—Inner surface with fine, woolly tomentum; margins of alternate sepals lined with fine, woolly tomentum; others lined with gland-tipped cilia.

*As first petal opens.*—Size—average. Form—Medium length to long; urn-shaped. Color: Outside—between Carmine, Plate 21/1, page 21 (Wilson) and Crimson, Plate 22/1, page 22 (Wilson); small area at base of petal near attachment near Uranium Green, Plate 63/3, page 63 (Wilson). Inside—between Geranium Lake, Plate 20/2, page 20 (Wilson) and Geranium Lake, Plate 20/1, page 20 (Wilson); small area at base of petal near attachment near Uranium Green, Plate 63/3, page 63 (Wilson).

*Opening.*—Opens up well; is not retarded from opening by cold, hot, wet or dry weather.

Bloom:

*Size (when fully open).*—Average to large; from 3½ inches to 4 inches in diameter.

*Petalage.*—Double; from 32 to 40 petals, plus 7 to 12 petaloids; arranged regularly.

*Form.*—High-centered and somewhat globular at first; becoming open to cupped later; petals at first being cupped, with lateral margins of inner petals usually reflexed slightly from ¼ to ⅓ of upper portion of petal; lateral margins of extreme outer petals usually reflexed ½ to ¾ or sometimes more of petal length; apex of outer petals sometimes reflexed ¼ to ½ of petal length; petals becoming later at maturity flat-cupped, with lateral margins of inner petals usually reflected ½ or more of upper portion of petal; lateral margins of extreme outer petals sometimes reflected ¾ or more of petal length; apex sometimes reflexed ½ or more of petal length.

Petals:

*Texture.*—Thick; leathery; with inside velvety and outside shiny to satiny.

*Shape.*—Outside—broadly obovate, with apex flat; sometimes with 1 or 2 notches. Intermediate—obovate, with apex rounded to flat; sometimes with 1 or 2 notches. Inside—narrowly obovate; somewhat irregular, with apex rounded; sometimes with 1 or 2 notches.

This description of a newly opened flower was made from a rose grown outdoors in the month of October, at Ontario, California:

Color:

*Outside petal.*—Outside surface—between Carmine, Plate 21/1, page 21 (Wilson) and Crimson, Plate 22/1, page 22 (Wilson); small area at base near attachment near Uranium Green, Plate 63/3, page 63 (Wilson). Inside surface—between Scarlet, Plate 19/1, page 19 (Wilson) and Geranium Lake, Plate 20/1, page 20 (Wilson); small area at base of petal near attachment near Uranium Green, Plate 63/3, page 63 (Wilson).

*Intermediate petal.*—Outside surface—between Carmine, Plate 21/1, page 21 (Wilson) and Crimson, Plate 22/1, page 22 (Wilson); small area at base of petal near attachment near Uranium Green, Plate 63/3, page 63 (Wilson). Inside surface—near Geranium Lake, Plate 20/1, page 20 (Wilson); small area at base of petal near attachment near Uranium Green, Plate 63/3, page 63 (Wilson).

*Inner petal.*—Outside surface—between Carmine, Plate 21/1, page 21 (Wilson) and Carmine, Plate 21, page 21 (Wilson); small area at base of petal near attachment near Uranium Green, Plate 63/3, page 63 (Wilson). Inside surface—near Geranium Lake, Plate 20/1, page 20 (Wilson); small area at base of petal near attachment near Uranium Green, Plate 63/3, page 63 (Wilson).

This description was made from a rose that was open for 3 days outdoors in the month of November, at Ontario, California:

Color:

*Outside petal.*—Outside surface—between Carmine, Plate 21/2, page 21 (Wilson) and Crimson, Plate 22/2, page 22 (Wilson); small area at base of petal near attachment near Uranium Green, Plate 63/3, page 63 (Wilson). Inside surface—between Geranium Lake, Plate 20/2, page 20 (Wilson) and Carmine, Plate 21/1, page 21 (Wilson); small area at base of petal near attachment near Uranium Green, Plate 63/3, page 63 (Wilson).

*Inside petal.*—Outside surface—between Carmine, Plate 21/1, page 21 (Wilson) and Crimson, Plate 22/1, page 22 (Wilson); small area at base of petal near attachment near Uranium Green, Plate 63/3, page 63 (Wilson). Inside surface—between Geranium Lake, Plate 20/2, page 20 (Wilson) and Geranium Lake, Plate 20/1, page 20 (Wilson); small area at base of petal near attachment near Uranium Green, Plate 63/3, page 63 (Wilson).

General color effect:

*Newly opened flower.*—Near Geranium Lake, Plate 20/1, page 20 (Wilson); small area at base of petals near Uranium Green, Plate 63/3, page 63 (Wilson).

*3-days open.*—Between Geranium Lake, Plate 20/2, page 20 (Wilson) and Geranium Lake, Plate 20/1, page 20 (Wilson); small area at base of petals near attachment near Uranium Green, Plate 63/3, page 63 (Wilson).

Behavior: Drop off cleanly; not particularly affected by cold, hot, wet or dry weather.

Flower longevity: On bush in garden—4 or 5 days in November. Cut roses grown outdoors and kept at living-room temperatures—5 days in November.

REPRODUCTIVE ORGANS

Stamens: Average number; arranged regularly about pistils; a few mixed with petaloids.

Filaments: Medium length to long; from 5 to 12 mm. in length; most with anthers.

*Color.*—Between Crimson, Plate 22/1, page 22 (Wilson) and Rose Madder, Plate 23/1, page 23 (Wilson).

Anthers: Medium size to large; all open approximately at once.

*Color.*—Upper side—margins near Buttercup Yellow, Plate 5/2, page 5 (Wilson); remainder near Aureolin, Plate 3/3, page 3 (Wilson); sometimes marked with near Rose Madder, Plate 23/2, page 23 (Wilson). Under side—margins near Buttercup Yellow, Plate 5/2, page 5 (Wilson); remainder near Aureolin, Plate 3/3, page 3 (Wilson); overlaid with near Rose Madder, Plate 23/2, page 23 (Wilson).

Pollen: Moderate to abundant.

*Color.*—Between Lemon Yellow, Plate 4/2, page 4 (Wilson) and Buttercup Yellow, Plate 5/2, page 5 (Wilson).

Pistils: Many; approximately 150 in number.

Styles: Moderately even; average length; from 4 to 8 mm. long; average caliper; bunched.

*Color.*—Upper 1/3 of style between Carmine, Plate 21/1, page 21 (Wilson) and Crimson, Plate 22/1, page 22 (Wilson); remainder near Uranium Green, Plate 63/3, page 63 (Wilson).

Stigma: Color—near Straw Yellow, Plate 604/2, page 67 (Wilson).

Ovaries: Usually all enclosed in calyx, but some protruding from calyx.

Hips: Average length; globular; smooth; walls thick and fleshy.

*Color (mature).*—Between Marigold Orange, Plate 11/1, page 11 (Wilson) and Orange, Plate 12/1, page 12 (Wilson).

Sepals: Permanent; medium length; somewhat curled and recurved.

*Color.*—Inside—between Courge Green, Plate XVII (Ridgway) and Biscay Green, Plate XVII (Ridgway), sometimes overlaid somewhat with near Indian Red, Plate XXVII (Ridgway) masked by white woolly tomentum. Outside—between Biscay Green, Plate XVII (Ridgway) and Light Elm Green, Plate XVII (Ridgway), sometimes overlaid with near Indian Red, Plate XXVII (Ridgway).

Seeds: Average number to many; from 17 to 25 in number; medium size.

PLANT

Foliage:

*Leaves.*—Compound of 3 to 5 to 7 leaflets; normal to abundant in quantity; medium size; leathery; semi-glossy.

*Leaflets.*—Shape—ovoid, with apex acute. Base—round. Margin—simply serrate.

*Color.*—Mature: Upper surface—near Dark Dull Yellow Green, Plate XXXII (Ridgway); under surface—near Chromium Green, Plate XXXII (Ridgway). Young: Upper surface—between Corinthian Purple, Plate XXXVIII (Ridgway) and Dark Corinthian Purple, Plate XXXVIII (Ridgway); under surface—between Corinthian Purple, Plate XXXVIII (Ridgway) and Neutral Red, Plate XXXVIII (Ridgway).

*Rachis (the supporting stem of the compound leaf).*—Average size. Upper side—grooved; with many stipitate glands on edges. Under side—prickly; with some stipitate glands.

*Stipules.*—Short to medium length; medium width to wide; with medium length points turning out at an angle of more than 45°.

*Disease resistance.*—Average resistance to mildew, as compared with other varieties grown under comparable cultural conditions at Ontario, California.

Growth:

*Habit.*—Bushy; upright; much-branched.

*Growth.*—Vigorous.

*Canes.*—Medium caliper to heavy.

*Main stems.*—Color—between Oil Green, Plate V (Ridgway) and Cedar Green, Plate VI (Ridgway). Large prickles—several to many; medium length; hooked slightly downward; with medium length, moderately narrow base. Color—near Wood Brown, Plate XL (Ridgway). Small prickles—several. Color—near Wood Brown, Plate XL (Ridgway). Hairs—none.

*Branches.*—Color—between Parrot Green, Plate VI (Ridgway) and Cedar Green, Plate VI (Ridgway). Large prickles—several; medium length; hooked slightly downward; with medium length, moderately narrow base. Color—near Sayal Brown, Plate XXIX (Ridgway). Small prickles—several. Color—near Sayal Brown, Plate XXIX (Ridgway). Hairs—none.

*New shoots.*—Color—near Absinthe Green, Plate

XXXI (Ridgway), overlaid with near Deep Corinthian Purple, Plate XXXVIII (Ridgway). Large prickles—several; medium length to long; hooked slightly downward, with moderately long, narrow base. Color—near Corinthian Purple, Plate XXXVIII (Ridgway). Small prickles—few to several. Color—near Corinthian Purple, Plate XXXVIII (Ridgway). Hairs—none.

I claim:

A new and distinct variety of rose plant of a class falling intermediate between the usual hybrid tea and hybrid polyantha classes, substantially as herein shown and described, characterized particularly as to novelty by the combination of the distinctive salmon red general color tonality of its blooms, the relatively large size and abundance of its blooms throughout the growing season, the excellent petal substance and attendant lasting quality of its blooms, the double petalage of its blooms, and its relatively long individual flower stems.

No references cited.